United States Patent
Koyama et al.

(10) Patent No.: US 9,945,799 B2
(45) Date of Patent: Apr. 17, 2018

(54) THERMAL DISPLACEMENT CORRECTION DEVICE FOR MACHINE TOOL

(71) Applicant: FANUC CORPORATION, Yamanashi (JP)

(72) Inventors: Yasuaki Koyama, Yamanashi (JP); Susumu Maekawa, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 373 days.

(21) Appl. No.: 14/670,719

(22) Filed: Mar. 27, 2015

(65) Prior Publication Data
US 2015/0276633 A1 Oct. 1, 2015

(30) Foreign Application Priority Data
Mar. 31, 2014 (JP) ................................. 2014-073564

(51) Int. Cl.
| | | |
|---|---|---|
| *G01N 25/16* | (2006.01) | |
| *G01M 99/00* | (2011.01) | |
| *G05B 19/404* | (2006.01) | |

(52) U.S. Cl.
CPC .......... *G01N 25/16* (2013.01); *G01M 99/002* (2013.01); *G05B 19/404* (2013.01); *G05B 2219/49207* (2013.01)

(58) Field of Classification Search
CPC ........ G05B 19/404; G05B 2219/49209; G05B 2219/49219; G05B 2219/49205–2219/49207
See application file for complete search history.

(56) References Cited

U.S. PATENT DOCUMENTS

| | | | | |
|---|---|---|---|---|
| 5,619,414 A | * | 4/1997 | Ishii ...................... | G05B 19/404 318/565 |
| 2002/0004688 A1 | * | 1/2002 | Kojima ................ | G05B 19/404 700/193 |
| 2012/0123586 A1 | * | 5/2012 | Maekawa ............ | G05B 19/404 700/173 |

FOREIGN PATENT DOCUMENTS

| | | |
|---|---|---|
| JP | 11-90779 A | 4/1999 |
| JP | 11-197998 A | 7/1999 |
| JP | 2002-018677 A | 1/2002 |
| JP | 2002-90135 A | 3/2002 |
| JP | 2009-251621 A | 10/2009 |
| JP | 2011-131371 A | 7/2011 |

(Continued)

OTHER PUBLICATIONS

Office Action in JP Application No: 2014-073564, dated Jan. 5, 2016.

(Continued)

*Primary Examiner* — Evan Pert
*Assistant Examiner* — Changhyun Yi
(74) *Attorney, Agent, or Firm* — Hauptman Ham, LLP

(57) ABSTRACT

A thermal displacement correction device for a machine tool is provided with detection result determination unit configured to determine, based on an actual position and a reference position detected by position detection unit, whether or not the actual position is based on correct detection, correction error calculation unit configured to calculate a correction error in the actual position if it is determined that the result of detection is based on correct detection, and correction amount modification unit configured to modify a thermal displacement correction amount based on the correction error.

9 Claims, 6 Drawing Sheets

(56) References Cited

FOREIGN PATENT DOCUMENTS

JP    2012-101330 A    5/2012

OTHER PUBLICATIONS

Office Action dated Sep. 29, 2015, corresponding to Japanese Patent Application No. 2014-073564.
Office Action in JP Application No. 2014-73564, dated Jul. 18, 2017, pp. 15.

* cited by examiner

THERMAL DISPLACEMENT CORRECTION DEVICE FOR MACHINE TOOL

RELATED APPLICATIONS

The present application claims priority to Japanese Application Number 2014-073564, filed Mar. 31, 2014, the disclosure of which is hereby incorporated by reference herein in its entirety.

BACKGROUND OF THE INVENTION

1. Field of the Invention

The present invention relates to a machine tool, and more particularly, to a thermal displacement correction device for the machine tool.

2. Description of the Related Art

Since a feed screw and a spindle of a machine tool are driven by a motor, they are expanded so that their mechanical positions change due to heating of the motor, frictional heat generated by the rotation of a bearing, and frictional heat from a contact portion between a ball screw and a ball nut of the feed screw. Thus, the relative positions of a workpiece to be positioned and a tool are shifted. The change of the mechanical positions due to heating hinders high-accuracy machining.

The displacement of the mechanical positions due to heating can be eliminated by using a technique in which a command position is corrected based on a displacement or temperature detected by a displacement or temperature sensor or a structure configured to apply an initial tension to the feed screw without being influenced by thermal expansion.

The technique for correcting the command position can be roughly classified into two categories.

In one of these categories, an actual thermal displacement is periodically detected for correction by using a touch probe, for example. In the other category, correction is made in real time by predicting a thermal displacement amount from a value detected by the sensor and the operating state of the machine tool. In these cases, accuracy and time are in a trade-off relationship. Accordingly, a method is proposed in which the overall accuracy of correction is improved by suitably detecting and modifying an actual thermal displacement amount, although the thermal displacement amount is basically predicted and corrected in real time.

According to Japanese Patent Application Laid-Open No. 2002-18677, a thermal displacement amount attributable to axial movement of a feed shaft is estimated for each of a finite number of sections into which the entire stroke of the feed shaft is divided. The distribution of thermal displacements in individual positions of a feed screw can be estimated by adding up the thermal displacement amounts for the sections from a reference position to a correction position. Thus, accurate correction can be made without regard to the position of the feed shaft. In addition, the thermal displacement can be accurately corrected in consideration of a thermal displacement due to heating of a spindle or spindle motor. Furthermore, more accurate correction is made by modifying a heating factor in a thermal displacement amount calculation formula, based on a deviation (correction error) between an estimated thermal displacement amount (correction amount) and an actual mechanical position.

According to Japanese Patent Application Laid-Open No. 2012-101330, an initial position is stored in advance by a position detection sensor and a position in which the next signal is output is detected as an actual position. An error correction factor is calculated based on the difference between the initial position and the detected actual position, whereby a thermal displacement amount is modified. Correction is made also in consideration of a change in ambient temperature or other thermal displacements irrelevant to machine operation.

According to Japanese Patent Application Laid-Open No. 11-90779, a thermal displacement amount is measured after the drive of a machine tool is started, and a calculated value of a thermal displacement correction amount is modified based on the measured value. Specifically, a difference obtained by subtracting the calculated value from the measured value or the ratio between the measured and calculated values is calculated as a correction value, and the thermal displacement amount is modified by adding the correction value to the calculated value or multiplying the calculated value by the correction value. An accurate thermal displacement amount can be calculated depending on various properties of the machine tool and the operating environment by modifying the calculated value of the thermal displacement amount based on the measured value.

According to Japanese Patent Applications Laid-Open Nos. 2002-18677, 2012-101330, and 11-90779, if chips are caught or a coolant splashes so that the result of detection by a position detection sensor is improper, a factor or thermal displacement correction amount may possibly be modified by mistake so that the result of correction becomes worse.

Disclosed in Japanese Patent Application Laid-Open No. 2002-18677, moreover, is the method for modifying the heating factor in the thermal displacement amount calculation formula based on the correction error. Since the calculation formula includes other factors or coefficients (a heat radiation coefficient and a heat conduction coefficient for calculating heat conduction from each adjacent section), the accuracy of the correction sometimes cannot be further improved by only modifying the heating factor.

In the technique disclosed in Japanese Patent Application Laid-Open No. 11-90779, moreover, the measured value of the thermal displacement amount is calculated by comparing a calculated drive amount with a drive amount obtained before a tool contacts a detector. If the calculated drive amount is different from the latter due to deformation of a column or the like, therefore, a problem remains that the thermal displacement cannot be satisfactorily corrected.

SUMMARY OF THE INVENTION

Accordingly, the object of the present invention is to provide a thermal displacement correction device for a machine tool, configured to perform re-detection if the result of detection by a position detection sensor is improper and modify a thermal displacement correction amount based on an accurately detected measured value of a thermal displacement amount (measured thermal displacement amount), thereby making correction also in consideration of a change in ambient temperature or other thermal displacements irrelevant to machine operation.

A thermal displacement correction device for a machine tool is configured to calculate a thermal displacement amount of the machine tool, set an amount for canceling the thermal displacement amount as a thermal displacement correction amount, and add the thermal displacement correction amount to a position command for a feed shaft, thereby making correction, and comprises a position detection unit configured to detect a position of a movable part of the machine tool, a reference position storage unit configured to store the result of detection by the position detection unit at a first point in time as a reference position, an actual position storage unit configured to store the result of detection by the position detection unit at a second point in time as an actual position, a detection result determination unit configured to determine, based on the actual position and the reference position, whether or not the actual position is based on correct detection, a re-detection unit configured to re-detect the position detected by the position detection unit if it is determined by the detection result determination unit that the detection result is not based on correct detection, a correction error calculation unit configured to compare the thermal displacement amount with an actual thermal displacement amount calculated from a difference between the actual position and the reference position and calculate a correction error in the actual position if it is determined by the detection result determination unit that the detection result is based on correct detection, and a correction amount modification unit configured to modify the thermal displacement correction amount based on the correction error calculated by the correction error calculation unit.

The detection result determination unit may be configured to determine the detection result to be based on correct detection if the difference between the actual position and the reference position is within a threshold value. Such an effect is obtained that it can be determined whether or not a detected value is based on correct measurement.

The threshold value may be obtained by addition of the thermal displacement amount. Such an effect is obtained that the threshold value need not be increased even in machining with large thermal displacement and false detection can be reduced.

The re-detection unit may be configured to perform detection after shifting a position of detection if it is determined by the detection result determination unit that the detection result is not based on correct detection. Such an effect is obtained that re-detection can be achieved even if chips are caught and prevent correct detection.

The correction amount modification unit may be configured to obtain an error correction factor from the ratio of the correction error to a thermal displacement amount in the actual position and increase or decrease the thermal displacement amount by multiplying or dividing the thermal displacement amount by the error correction factor. Such an effect is obtained that the correction amount can be modified by a ratio.

The correction amount modification unit may be configured to add or subtract a value, obtained by subtracting the thermal displacement amount in the actual position from the correction error in the actual position, to or from the thermal displacement amount, to increase or decrease the thermal displacement amount. Such an effect is obtained that the correction amount can be modified by a difference.

According to the present invention configured as described above, there can be provided a thermal displacement correction device for a machine tool, configured to perform re-detection if the result of detection by a position detection sensor is improper and modify a thermal displacement correction amount based on an accurately detected measured thermal displacement amount, thereby making correction also in consideration of a change in ambient temperature or other thermal displacements irrelevant to machine operation.

BRIEF DESCRIPTION OF THE DRAWINGS

The above and other objects and features of the present invention will be obvious from the ensuing description of embodiments with reference to the accompanying drawings, in which.

DETAILED DESCRIPTION OF THE PREFERRED EMBODIMENTS

A method of detecting the position of a feed shaft will be described first.

1. <Position Detection Sensor (for Detection of Feed Shaft Position)>

Figure 1:
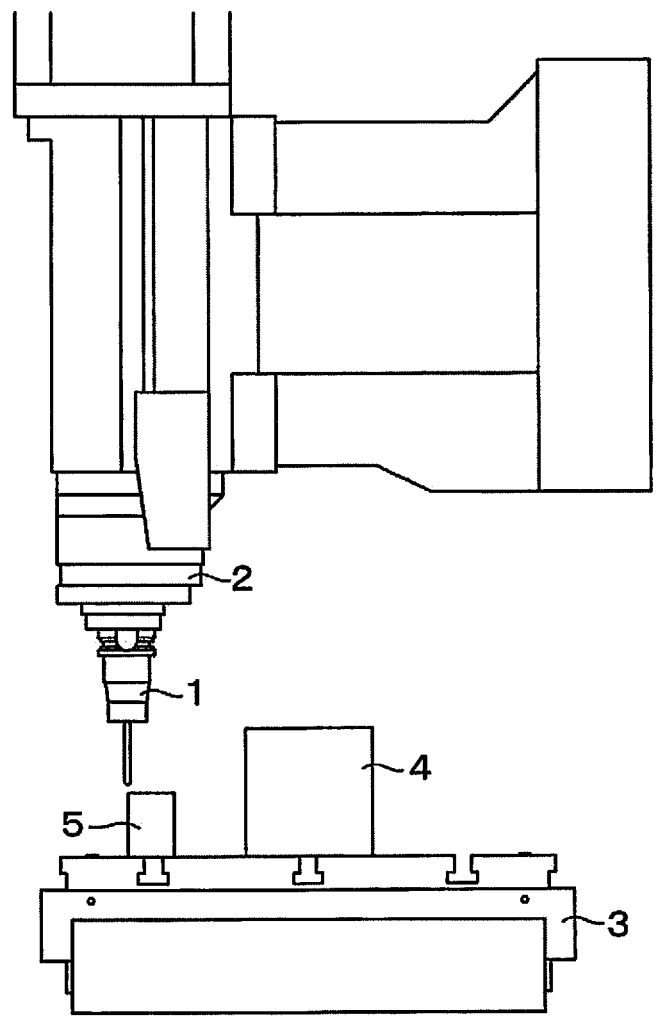
FIG. 1 is a view showing an example of the installation position of a position detection sensor.

FIG. 1 is a schematic view showing an example of the installation position of a position detection sensor 1. As shown in FIG. 1, the position detection sensor 1 is held on a spindle 2 and generates a contact signal when it is brought into contact with a jig 5 or a workpiece 4 fixed on a table 3. For example, a touch probe (or touch-type probe) is used as the position detection sensor 1. Since the touch probe also moves as the feed shaft of a machine tool moves, it can make detection from an optimal position and in an optimal direction.

The position detection sensor 1 is not limited to the touch probe described above, and may alternatively be a contact-type position detection switch such as a limit switch, microswitch, etc., or a non-contact position detection switch such as a magnetic detection switch, inductive proximity switch, capacitive proximity switch, etc.

For the installation position, moreover, a detection head may be set on a stationary part of a machine body, and a magnetism generating body may be mounted on a movable part of the machine body. The stationary part may be, for example, a bed, column, or saddle of the machine tool, which is immovable relative to each feed shaft. The movable part may be, for example, a spindle head, table, saddle, or nut in threaded engagement with one of the feed shafts, which is movable along each feed shaft.

Figure 2:
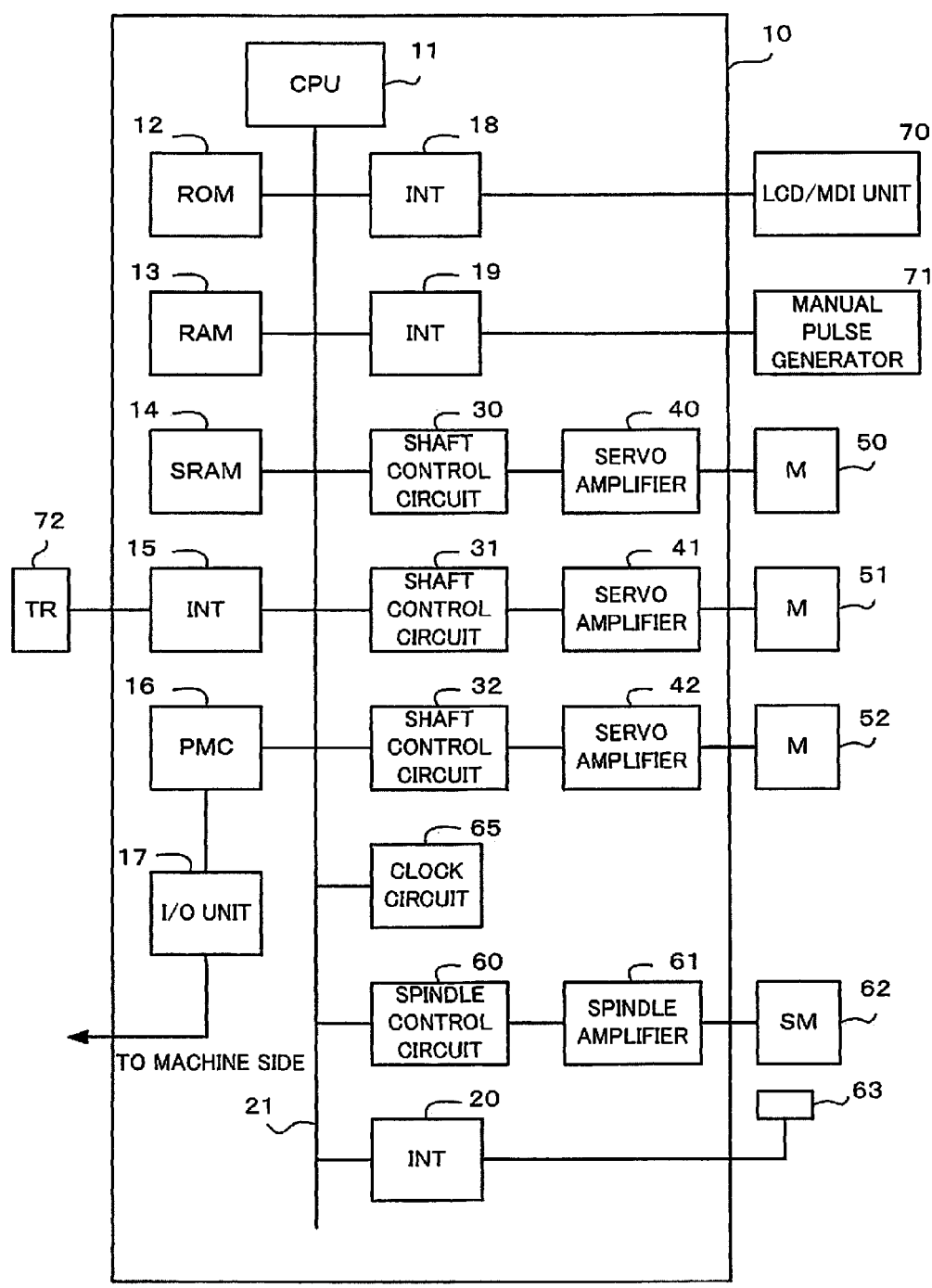
FIG. 2 is a block diagram showing a principal part of a numerical controller for controlling a machine tool.

FIG. 2 is a functional block diagram showing a principal part of a numerical controller for the machine tool. A processor (CPU) 11 of a numerical controller 10 serves to totally control the numerical controller 10. The processor 11 reads a system program stored in a ROM 12 through a bus 21, and totally controls the numerical controller 10 in accordance with the read system program. A RAM 13 is stored with temporary calculation data, display data, and various data input by an operator through an LCD/MDI unit 70.

An SRAM 14 is constructed as a nonvolatile memory that is backed up by a battery (not shown) so that it can maintain its storage state even after the numerical controller 10 is powered off. The SRAM 14 can be stored with a program for the measurement of an initial position, program for thermal displacement correction of the machine tool, machining program (described later) read through an interface 15, machining program input through the LCD/MDI unit 70, and other programs. Further, the ROM 12 is preloaded with various system programs for the execution of edit-mode processing required for the creation and editing of the machining program and processing for automatic operation.

The interface 15 serves for external equipment that can be connected to the numerical controller 10 and is connected with an external device 72, such as an external storage device. The machining program, thermal displacement measurement program, and other programs are read from the external storage device. A programmable machine controller (PMC) 16 controls auxiliary devices or the like on the machine tool side by sequential programs in the numerical controller 10. Necessary signals on the auxiliary device side are converted according to these sequential programs based on M-, S-, and T-functions commanded by the machining program. The converted signals are output to the auxiliary device side through an I/O unit 17. The various auxiliary devices, e.g., actuators, are activated by these output signals. When signals are received from various switches of a control panel on the machine tool body, moreover, they are processed as required and delivered to the processor 11.

Image signals indicative the current position of each axis of the machine tool, alarms, parameters, image data, etc., are delivered to the LCD/MDI unit 70 and displayed on its display. The LCD/MDI unit 70 is a manual data input device provided with a display, keyboard, etc. An interface 18 receives data from the keyboard of the LCD/MDI unit 70 and delivers it to the processor 11.

An interface 19 is connected to a manual pulse generator 71. The manual pulse generator 71 is mounted on the control panel of the machine tool and used to precisely position movable parts of the machine tool by each-axis control with distributed pulses based on manual operation. X-, Y-, and Z-axis control circuits 30 to 32 for moving a table T of the machine tool receive move commands from the individual axes from the processor 11 and output the commands to servo amplifiers 40 to 42, respectively. On receiving these commands, the servo amplifiers 40 to 42 drive servomotors 50 to 52 for the individual axes of the machine tool, respectively. Pulse coders for position detection are incorporated in the servomotors 50 to 52, individually. Position signals from these pulse coders are fed back as pulse trains.

A spindle control circuit 60 receives a spindle rotation command for the machine tool and outputs a spindle speed signal to a spindle amplifier 61. On receiving this spindle speed signal, the spindle amplifier 61 rotates a spindle motor 62 of the machine tool at a commanded rotational speed, thereby driving a tool. A position coder 63 is coupled to the spindle motor 62 by gears, a belt, or the like. The position detector 63 outputs feedback pulses in synchronism with the rotation of the spindle, and the feedback pulses are read through an interface 20 by the processor 11. Numeral 65 denotes a clock circuit adjusted so as to synchronize with the current time. Processing of the flowchart described below is performed by the numerical controller 10.

The following is a description of an embodiment.

2. <Estimation and Correction of Thermal Displacement Amount>

2.1<Section Setting>

Figure 3:
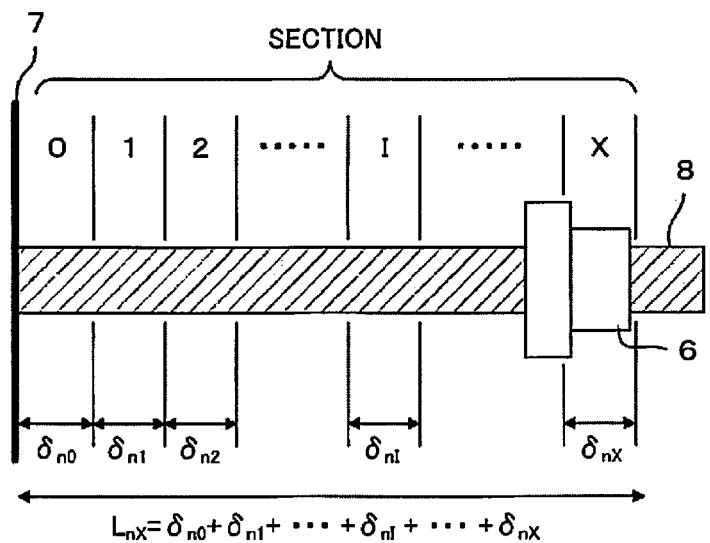
FIG. 3 is a diagram illustrating section setting.

Calculation and correction of a thermal displacement amount will be described first. The thermal displacement amount of the feed shaft is estimated by the same method as that disclosed in Japanese Patent Application Laid-Open No. 2002-18677. First, as shown in FIG. 3, the entire length (stroke) of a feed screw 8 constituting the feed shaft is divided into a plurality of sections (Sections 0 to X) set with the position of a fixed bearing as a reference position 7.

The entire length of the feed screw 8 is assumed to cover a movable range from the end face of the fixed bearing on the side of a nut 6, as a reference position, to the end face on the side at least farther from the reference position of the nut 6. The entire length of the feed screw 8 is divided into a finite number of sections, the section adjacent to the reference position is assumed to be Section 0, and the section farthest from the reference position is assumed to be Section X.

As for a thermal displacement amount (hereinafter referred to as "feed-shaft-section thermal displacement amount") in Position X caused by thermal displacement of the feed shaft when the entire length of the feed screw 8 is divided into a number, X, of sections, a feed-shaft-section thermal displacement amount LnX for Section X at Time n can be obtained by adding up the thermal displacement amounts for the individual sections from the reference position 7 to Section X, as indicated by equation (1) as follows:

$$LnX = \delta n0 + \delta n1 + \ldots + \delta nI + \ldots + \delta nX, \quad (1)$$

where $\delta nI$ is a thermal displacement amount for Section I (arbitrary section) and LnX is the feed-shaft-section thermal displacement amount in Section X at time n.

2.2<Correction of Thermal Displacement>

The following is a description of correction of thermal displacement. The thermal displacement is corrected for each predetermined short period (e.g., for each 4 ms) with reference to the flowchart of FIG. 4. First, the position of the feed shaft is detected and stored into the memory. A modified feed-shaft-section thermal displacement amount LnI' for a section (Section I) corresponding to the detected position of the feed shaft is read from the memory and an amount for canceling it is assumed to be a thermal displacement correction amount. Thus, the modified feed-shaft-section thermal displacement amount LnI' is negatively equal to the thermal displacement correction amount. Accordingly, the correction is made by adding the thermal displacement correction amount to a position command for the feed shaft.

Figure 4:
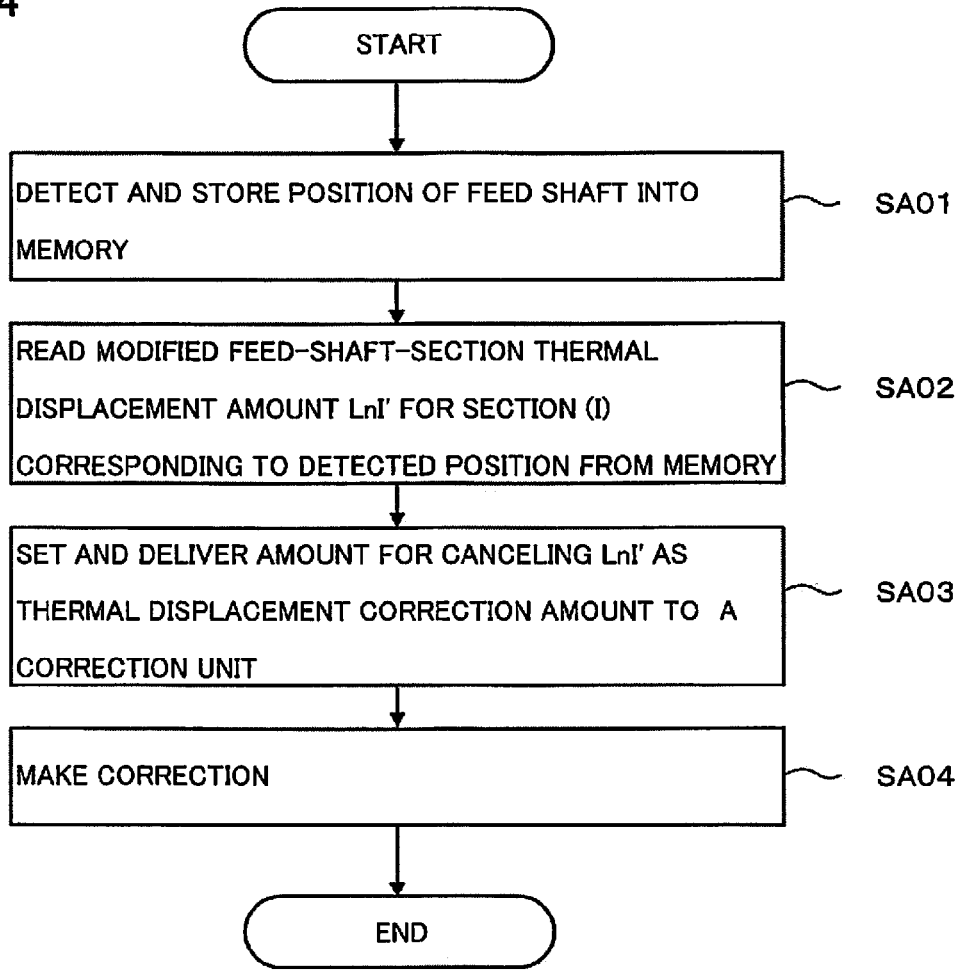
FIG. 4 is a flowchart showing processing for thermal displacement correction.

The following is a sequential description of various steps of operation shown in the flowchart of FIG. 4.

[Step SA01] The position of the feed shaft is detected and stored into the memory.

[Step SA02] The modified feed-shaft-section thermal displacement amount LnI' for Section I corresponding to the detected position is read from the memory. The modified feed-shaft-section thermal displacement amount LnI' will be described later.

[Step SA03] The amount for canceling the modified feed-shaft-section thermal displacement amount LnI' is assumed to be the thermal displacement correction amount and delivered to a correction unit.

[Step SA04] Correction is made, whereupon the processing ends.

2.3<Calculation of Thermal Displacement Amount>

Figure 5:
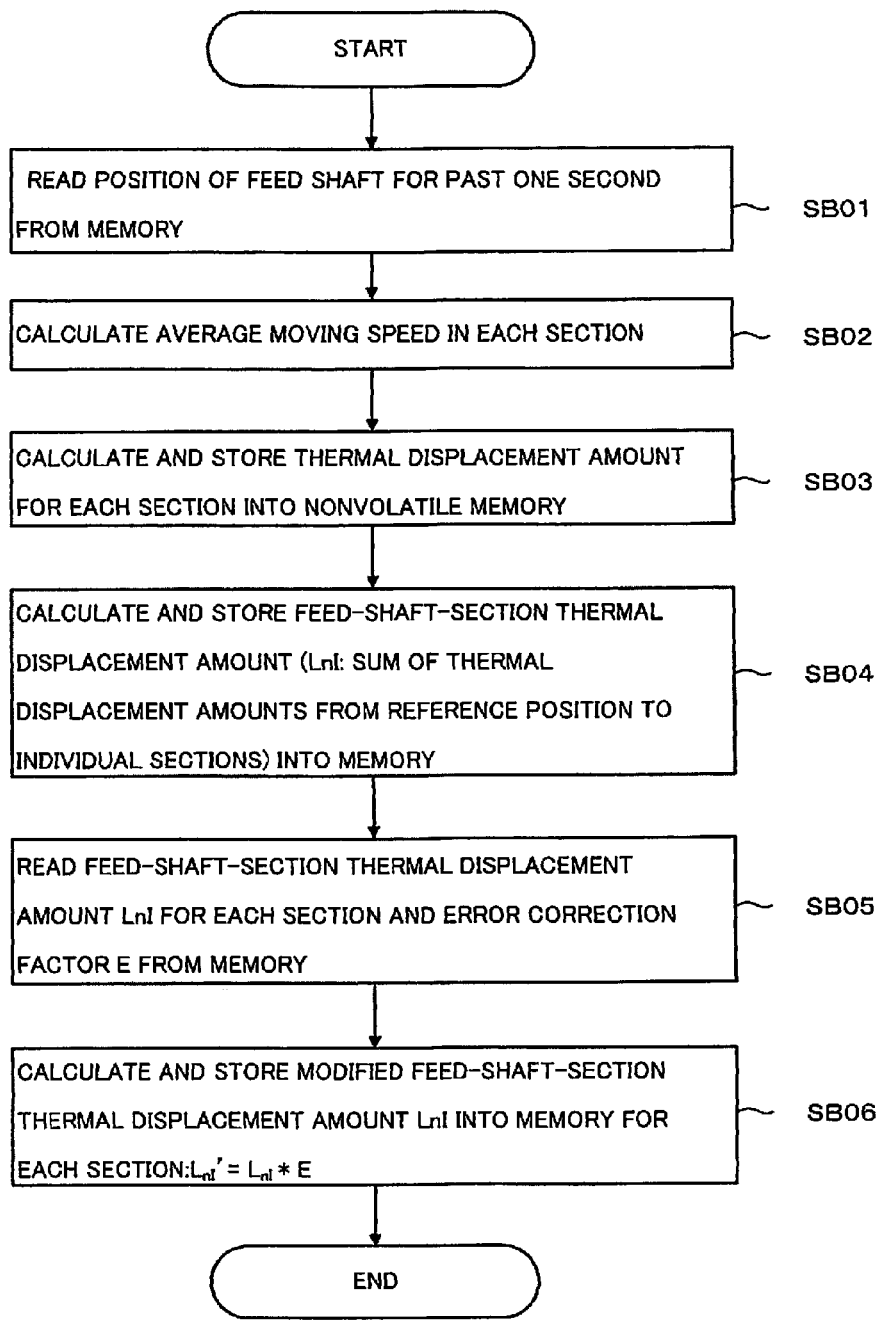
FIG. 5 is a flowchart showing processing for calculating a thermal displacement amount.

The thermal displacement amount is calculated for each predetermined period (e.g., for each second) in the manner shown in the flowchart of FIG. 5. The following is a sequential description of various steps of operation shown in the flowchart of FIG. 5.

[Step SB01] The position of the feed shaft stored in the memory in the processing of FIG. 4 is read for the past one second from the memory.

[Step SB02] An average moving speed in each section is obtained from the position of the feed shaft read from the memory.

[Step SB03] The thermal displacement amount for each section is obtained from the average movement speed in each section and stored into the nonvolatile memory.

[Step SB04] A feed-shaft-section thermal displacement amount LnI for each section is obtained by adding up the thermal displacement amounts for the individual sections from the reference position to each section based on equation (1) and stored into the memory. For example, the memory is stored with Ln0=δn0 as a feed-shaft-section thermal displacement amount for Section 0, Ln1=δn0+δn1 as a feed-shaft-section thermal displacement amount for Section 1, and Ln 2=δn0+δn1+δn2 as a feed-shaft-section thermal displacement amount for Section 2.

[Step SB05] The feed-shaft-section thermal displacement amount LnI for each section and an error correction factor E are read from the memory.

[Step SB06] Based on the feed-shaft-section thermal displacement amount LnI and the error correction factor E, the modified feed-shaft-section thermal displacement amount LnI' obtained by the modification of the feed-shaft-section thermal displacement amount by equation (2) is stored into the memory for each section, whereupon the processing ends.

$$LnI'=LnI \cdot E. \tag{2}$$

2.4<Calculation of Error Correction Factor E>

Figure 6:
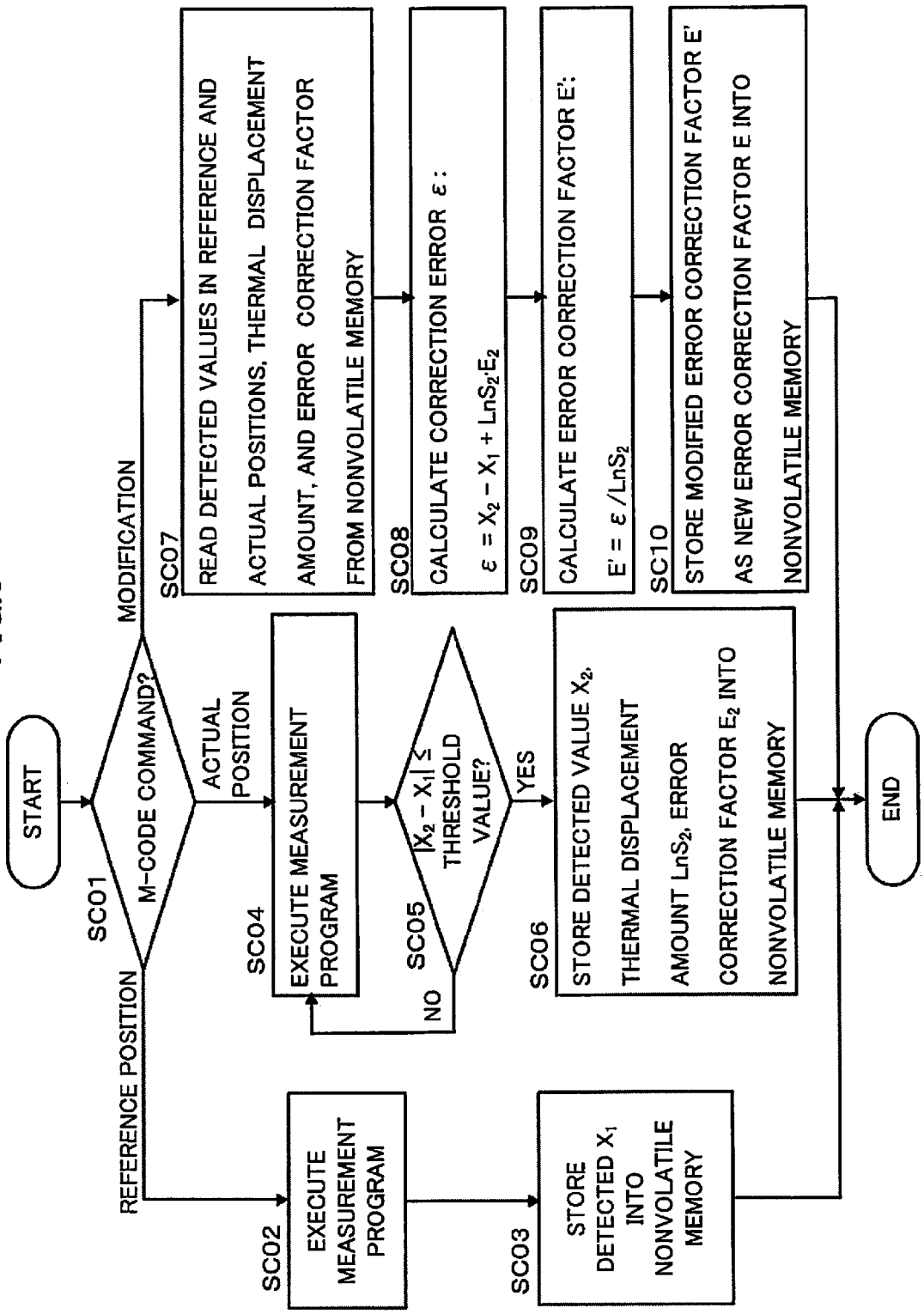
FIG. 6 is a flowchart showing processing for calculating an error correction factor E.

The following is a description of a method of calculating the error correction factor E. The error correction factor E is calculated as the operator issues a command at an arbitrary timing in the machining program using an M-code or inputs a detected value to its dedicated screen at an arbitrary timing after machining. This calculation is performed with reference to the flowchart of FIG. 6. The following is a sequential description of various steps of operation shown in the flowchart of FIG. 6.

[Step SC01] A decision is made on the next processing in response to the command based on the M-code. If the reference position is commanded by an argument, the processing proceeds to Step SC02. If an actual position is commanded by an argument, the processing proceeds to Step SC04. If modification of the error correction factor is commanded by an argument, the processing proceeds to Step SC07. The determination of conditions is not limited to the commanding based on the M-code and may be executed on condition that a cursor is moved to each item provided on a dedicated screen.

[Step SC02] The measurement program is executed to cause the position detection sensor to detect the reference position. Alternatively, the operator manually moves the feed shaft to cause the position detection sensor to detect the reference position and inputs the detected value to the dedicated screen.

[Step SC03] A detected value $X_1$ in the reference position is stored into the nonvolatile memory. This reference position may or may not be subjected to thermal displacement correction before the storage. When the storage is completed, the processing ends.

[Step SC04] The measurement program is executed to cause the position detection sensor to detect the actual position. The same position command for the detection of the reference position is used for the detection of the actual position. Alternatively, the operator manually moves the feed shaft to cause the position detection sensor to detect the actual position and inputs the detected value to the dedicated screen.

[Step SC05] It is determined whether a difference $|X_2-X_1|$ between detected values $X_2$ and $X_1$ in the actual and reference positions is not larger than a threshold value T. If the difference is not larger than the threshold value T, the processing proceeds to Step SC06. If the difference is larger than the threshold value T, the processing proceeds to Step SC04, whereupon the measurement program is performed again (for re-detection).

The threshold value T includes the thermal displacement amount, as indicated by equation (3). In this equation, α and β are preset factors. The factor α is determined depending on the size of chips, while the factor β represents the inaccuracy of the thermal displacement correction. If the thermal displacement correction is not accomplished, 1 is loaded into β. If the thermal displacement correction is accomplished with little environmental change, a value close to 0 is loaded into β. Further, $LnS_2$ is a thermal displacement amount in a section (Section $S_2$) to which the detected actual position belongs.

$$T=\alpha+\beta \cdot LnS_2. \tag{3}$$

Figure 7A:
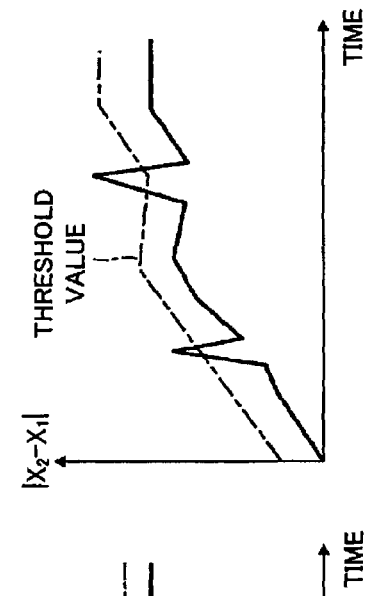
FIGS. 7A and 7B are diagrams for illustrating equation (3)
Figure 7B:
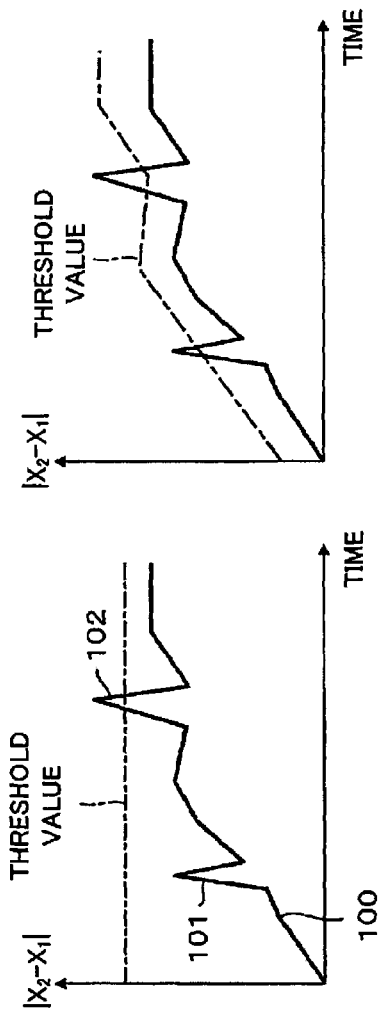

The significance of equation (3) will be described with reference to FIGS. 7A and 7B. Numeral 100 designates a graph prepared by plotting the elapsed time for $|X_2-X_1|$. The difference $|X_2-X_1|$ varies as the thermal displacement is changed by machining. Chips are caught and cause $|X_2-X_1|$ to suddenly increase when values denoted by numerals 101 and 102 in this graph are detected, and false values should preferably be identified at these points in time of detection. FIG. 7A shows a case where the threshold value is constant. If the threshold value is set so that the value 102 is determined to be false, the value 101 is not identified. If the threshold value is set so that the value 101 is determined to be false, in contrast, a false value is inevitably identified despite normal detection. FIG. 7B shows a case where the threshold value includes the thermal displacement amount. Since the threshold value changes in agreement with the thermal displacement, both the values 101 and 102 can be determined to be false.

In order to keep away from chips during the re-detection, the position of detection is shifted by adding a preset value γ to a command position in the measurement program. The value γ is determined depending on the size of the chips.

[Step SC06] The detected value $X_2$ in the actual position, the unmodified thermal displacement amount $LnS_2$ in Section $S_2$ to which the detected actual position belongs, and an error correction factor $E_2$ are stored into the nonvolatile memory. This actual position may or may not be subjected to thermal displacement correction before the storage. If the thermal displacement correction is not accomplished, 0 is stored into the nonvolatile memory for the error correction factor $E_2$. When the storage is completed, the processing ends.

Normally, modification of the error correction factor is ordered immediately after the detection of the actual position is finished.

[Step SC07] The detected value $X_1$ in the reference position, detected value $X_2$ in the actual position, thermal displacement amount $LnS_2$, and error correction factor $E_2$ are read from the nonvolatile memory.

[Step SC08] A correction error ε in the actual position is obtained by equation (4) based on the difference between the detected values $X_2$ and $X_1$ in the actual and reference positions, in consideration of the thermal displacement amount, as follows:

$$\epsilon=X_2-X_1+LnS_2 \cdot E_2. \tag{4}$$

[Step SC09] A modified error correction factor E' is obtained by equation (5) based on the thermal displacement amount $LnS_2$ and the correction error $\epsilon$ in the actual position, as follows:

$$E'=\epsilon/LnS_2. \quad (5)$$

Figure 8A:
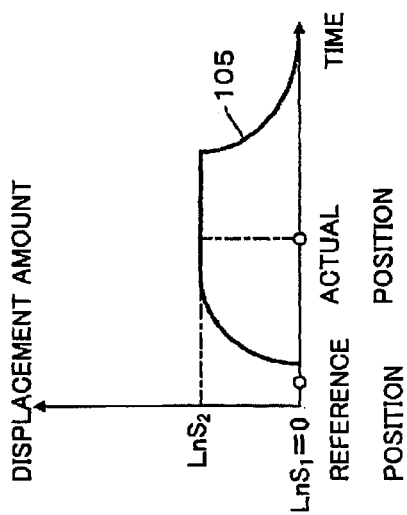
FIGS. 8A and 8B are diagrams for illustrating equations (4) and (5).
Figure 8B:
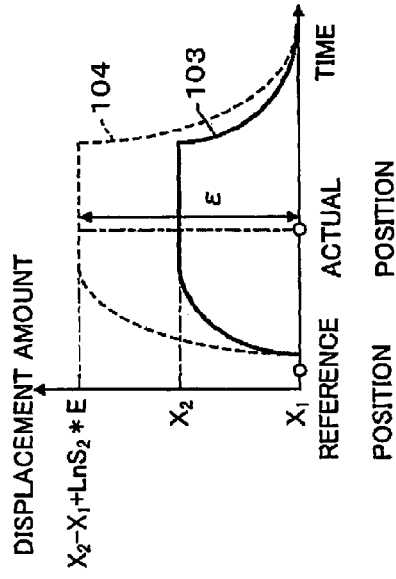

The significance of equations (4) and (5) will be described with reference to FIGS. 8A and 8B. For simplicity, let us assume that the detected value $X_1$ in the reference position and a thermal displacement amount $LnS_1$ in Section $S_1$ to which the detected reference position belongs are 0 and the error correction factor $E_2$ in the actual position is 1. A graph 103 is assumed to be obtained by plotting detected values. Since the detected values are values obtained after correction by a thermal displacement amount denoted by numeral 105, the actual thermal displacement amount can be represented by a graph 104. In particular, the actual thermal displacement amount in the actual position is the correction error $\epsilon$ in equation (4). According to equation (5), the modified error correction factor E' is obtained such that a modified thermal displacement amount $LnS_2 \cdot E'$ in the actual position is equal to the correction error $\epsilon$.

[Step SC10] The modified error correction factor E' obtained in Step SC09 is stored as a new error correction factor E into the nonvolatile memory, whereupon the processing end.

Since the error correction factor E is updated based on the measured thermal displacement amount detected by the position detection sensor as in Step SC09, high-accuracy correction can be achieved also in consideration of a change in ambient temperature or other thermal displacements irrelevant to machine operation.

The touch probe mounted on the spindle can be used to detect deformation of castings due to heating of the spindle, including tilting of a spindle mount or a column. Therefore, a value based on addition of the thermal displacement amount, as well as the feed-shaft-section thermal displacement amount LnI, may be used in the calculation of the thermal displacement amount and the like in Items 2.2 and 2.3.

In Item 2.4, moreover, the error correction factor E is calculated from the correction error $\epsilon$ and the thermal displacement amount $LnS_2$ in the actual position, as indicated by equation (5). Alternatively, however, the error correction factor E may be calculated from a difference, as indicated by equation (6) as follows:

$$E'=\epsilon-LnS_2. \quad (6)$$

In this case, equation (2) in Item 2.3 is replaced by equation (7) as follows:

$$LnI'=LnI+E. \quad (7)$$

If the difference $|X_2-X_1|$ between the detected values $X_1$ and $X_2$ in the reference and actual positions is larger than the threshold value, an alarm may be generated to stop the automatic operation. If the difference is larger than the threshold value in any of cycles of re-detection repeated at a preset frequency, moreover, an alarm may be generated to stop the automatic operation. If no chips are caught at the detection position and if the position detection sensor has no problem, the operator can determine that the possibility of the detected value in the reference position not being based on correct detection is high.

At the time of the re-detection, it is highly possible that accurate detection can be performed even in the same position as chips are touched by the touch probe and fall. However, the possibility of accurate detection can be further increased by using the method of shifting the detection position. Alternative re-detection methods include a method in which a coolant and air are discharged into the detection position, a method in which a position detection sensor based on a different detection mechanism is used as an alternative, and a method in which the detection position is shifted from the jig side by, for example, rotating a cylindrical jig on an additional shaft.

According to the embodiment described above, the thermal displacement correction amount is modified based on the measured thermal displacement amount. Thus, an accurate thermal displacement correction amount can be calculated also in consideration of a change in ambient temperature, various properties of the machine tool, or other thermal displacements irrelevant to machine operation.

The thermal displacement amount is corrected based on the prediction from the operating state of the machine tool. Thus, accurate correction can be made in real time by only detecting the thermal displacement at key points where the ambient environment changes, not by periodically detecting the thermal displacement by the position sensor and extending the machining time.

Further, the detection in the reference position can be performed at an arbitrary timing and the thermal displacement correction amount can be modified based on an arbitrary machine state. For example, the thermal displacement occurs due to a change in ambient temperature or the like even without machining, so that the influence of the thermal displacement having occurred before the machining can be reduced by detecting the reference position immediately before the machining.

Furthermore, the thermal displacement correction amount can be modified by using an accurate detected value. In identifying a false value by a threshold value, the detected value is changed by the thermal displacement. Although it is difficult to determine a constant threshold value, therefore, the threshold value can be set to a constant value according to the above-described embodiment. If the false value is identified, re-detection is performed after shifting the detection position. Even when chips are caught, therefore, the possibility of accurate detection being achieved next time is high.

The invention claimed is:

1. A thermal displacement correction device for a machine tool for machining a work, the thermal displacement correction device is configured to calculate a thermal displacement amount of the machine tool, set an amount for canceling the thermal displacement amount as a thermal displacement correction amount, and add the thermal displacement correction amount to a position command for a feed shaft, thereby making correction, the thermal displacement correction device comprising:
   a position detection sensor configured to detect a position of a movable part of the machine tool;
   a reference position storage configured to store the result of detection by the position detection sensor at a first point in time as a reference position;
   an actual position storage configured to store the result of detection by the position detection sensor at a second point in time as an actual position; and
   a numerical control device including a processor configured to
      determine, based on the actual position and the reference position, whether or not the actual position is based on correct detection, re-detect the position detected by the position detection sensor when it is determined that the detection result is not based on correct detection, compare the thermal displacement amount with an actual thermal displacement amount calculated from a difference between the actual position and the reference position and calculate a correction error in the actual position when it is determined that the detection result is based on correct detection, modify the thermal displacement correction amount based on the calculated correction error, and correct the position command for the feed shaft based on the modified thermal displacement correction amount, to control the feed shaft for positioning the movable part which is engaged with and movable along the feed shaft.

2. The thermal displacement correction device according to claim 1, wherein the processor is configured to determine the detection result to be based on correct detection when the difference between the actual position and the reference position is within a threshold value.

3. The thermal displacement correction device according to claim 2, wherein the processor is configured to obtain the threshold value by using the thermal displacement amount.

4. The thermal displacement correction device according to claim 2, wherein the processor is configured to change the threshold value in proportion to the difference between the actual position and the reference position, when the difference is varied as the thermal displacement is changed by machining.

5. The thermal displacement correction device according to claim 2, wherein when the difference between the actual position and the reference position is larger than the threshold value, the processor is configured to generate an alarm and stop an automatic operation of the machine tool.

6. The thermal displacement correction device according to claim 2, wherein when the difference is larger than the threshold value in any of cycles of re-detection repeated at a preset frequency, the processor is configured to generate an alarm and stop an automatic operation of the machine tool.

7. The thermal displacement correction device according to claim 1, wherein the processor is further configured to perform detection after shifting a position of detection when the processor determines that the detection result is not based on correct detection.

8. The thermal displacement correction device according to claim 1, wherein the processor is further configured to obtain an error correction factor from the ratio of the correction error to a thermal displacement amount in the actual position, and increase or decrease the thermal displacement amount by multiplying or dividing the thermal displacement amount by the error correction factor.

9. The thermal displacement correction device according to claim 1, wherein the processor is further configured to add or subtract a value, obtained by subtracting the thermal displacement amount in the actual position from the correction error in the actual position, to or from the thermal displacement amount, to increase or decrease the thermal displacement amount.

* * * * *